United States Patent
Ramsay et al.

(10) Patent No.: US 6,750,178 B1
(45) Date of Patent: Jun. 15, 2004

(54) AGROCHEMICAL COMPOSITION

(75) Inventors: Julia Lynne (nee Cutler) Ramsay, Bracknell (GB); Antony George Seville, Bracknell (GB); Michael John Bean, Greensboro, NC (US)

(73) Assignee: Syngenta Limited (GB)

( * ) Notice: Subject to any disclaimer, the term of this patent is extended or adjusted under 35 U.S.C. 154(b) by 0 days.

(21) Appl. No.: 09/937,762

(22) PCT Filed: Mar. 21, 2000

(86) PCT No.: PCT/GB00/01062
§ 371 (c)(1),
(2), (4) Date: Jan. 29, 2002

(87) PCT Pub. No.: WO00/59302
PCT Pub. Date: Oct. 12, 2000

(30) Foreign Application Priority Data

Apr. 1, 1999 (GB) ............................................... 9907669

(51) Int. Cl.$^7$ ......................... A01N 25/30; A01N 57/02; A01N 43/58
(52) U.S. Cl. ......................... 504/206; 504/237; 504/250; 504/337; 504/365
(58) Field of Search ................................ 504/206, 237, 504/250, 337, 365

(56) References Cited

U.S. PATENT DOCUMENTS

| | | | |
|---|---|---|---|
| 5,688,085 A | | 11/1997 | Watts |
| 6,117,820 A | * | 9/2000 | Cutler et al. ............ 504/206 |

FOREIGN PATENT DOCUMENTS

| | | | |
|---|---|---|---|
| EP | 0 375 624 | * | 6/1990 |
| WO | 96/32839 | | 10/1996 |
| WO | 97/32476 | | 9/1997 |

OTHER PUBLICATIONS

Huntsman. Technical Bulletin: The JEFFAMINE® polyoxyalkyleneamines. p. 1–6. 1987.*
Wyrill, J.B. et al., "Glyphosphate Toxicity to Common Milkweed and Hemp Dogbane as influenced by Surfactants," Weed Science, U.S., Weed Science Society of America, Champaign, IL, vol. 25, No. 3, May 1977, pp 275–287.
Jeffamine Data Sheet D–Series, no date.
Jeffamine Data Sheet ED–Series, no date.
Jeffamine Data Sheet XTJ–504 (EDR–148), no date.
Jeffamine Data Sheet M–Series, no date.
Jeffamine Data Sheet T–403, no date.

* cited by examiner

Primary Examiner—S. Mark Clardy
(74) Attorney, Agent, or Firm—Thomas Hamilton

(57) ABSTRACT

An aqueous agrochemical composition comprises an agrochemical active ingredient such as glyphosate, paraquat or fomesafen and an adjuvant of formula (I): $X-(R^3O)_a-R^4-NR^2R^1$ and salts thereof, wherein $R^1$ and $R^2$ are independently hydrogen or a lower alkyl group or a group $X-(R^3O)_a-R^4-$ wherein X is $-OH$ or a lower alkoxy group; $R^3O$ is an ethoxy, propoxy or butoxy group or a random or block mixture thereof; $R^4$ is a linear or branched chain alkylene bridging group containing from 1 to 4 carbon atoms; X is (IA)—OH or a lower alkyloxy group; or (IB) a group $R^5R^6N-$ or $R^5R^6N-R^7-$; or (IC) a group (I) wherein a, is from 1 to 400 or if X is of formula IC, the sum of a, b and c is from 3 to 400 and d is 0 or 1.

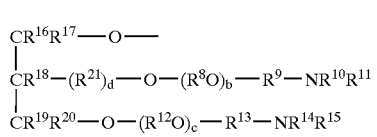

(1)

16 Claims, No Drawings

AGROCHEMICAL COMPOSITION

This application is a 371 of International Application No. PCT/GB00/01062 filed Mar. 21, 2000, which claims priority to GB9907669.7, filed Apr. 1, 1999, the contents of which are incorporated herein by reference.

This invention relates to an agrochemical composition and in particular to an agrochemical composition containing an activity-enhancing adjuvant.

An agrochemical is generally used with an adjuvant or combination of adjuvants to provide optimum biological activity. Much has been published on the selection of adjuvants to achieve particular effects with individual agrochemicals and classes of agrochemical. In general it has been assumed that activity-enhancement results from surfactant properties of the adjuvant and most such activity-enhancing adjuvants are surfactants in that they contain within the molecule both a hydrophobic portion and a-lypophobic-portion. We have now found that a class of alkoxylated amines provides excellent activity enhancement when used in an agrochemical formulation. Surprisingly certain members of the class have either no surfactant properties or low surfactant properties. Furthermore, unlike many surfactants used as conventional agrochemical adjuvants, the alkoxylated amines of the present invention generally exhibit an exceptionally low toxicological profile and in particular excellent ecotoxicological characteristics and provide compositions which are especially benign to the environment. It is exceptional to find adjuvants which combine a high level of activity enhancement with low toxicity.

According to the present invention there is provided an agrochemical composition comprising an agrochemical active ingredient and an adjuvant of formula (I) and salts thereof $$X-(R^3O)_a-R^4-NR^2R^1 \quad (I)$$

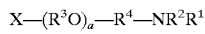

wherein $R^1$ and $R^2$ are independently hydrogen or a lower alkyl group or a group $X'-(R^{3'}O)_{a'}-R^{4'}-$ wherein $R^{3'}$ and $R^{4'}$ respectively may take any of the values of $R^3$ and $R^4$ as hereinafter defined and wherein X' is —OH or a lower alkoxy group containing from 1 to 6 carbon atoms and a' is from 0 to 400

$R^3O$ is an ethoxy, propoxy or butoxy group or a random or block mixture thereof, $R^4$ is a linear or branched chain alkylene bridging group containing from 1 to 4 carbon atoms, X is (IA) —OH or a lower alkoxy group containing from 1 to 6 carbon atoms or X is (IB) a group $R^5R^6N-$ or $R^5R^6N-R^7-$ wherein $R^5$ and $R^6$ are independently hydrogen or a lower alkyl group or a group $X'-(R^{3'}O)_{a'}-R^{4'}-$ as hereinbefore defined wherein X' is —OH or a lower alkoxy group containing from 1 to 6 carbon atoms, and $R^7$ is a linear or branched chain alkylene bridging group containing from 1 to 4 carbon atoms or X is (IC) a group

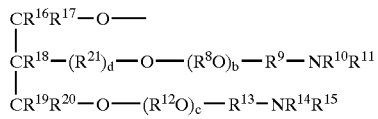

wherein $R^{10}$, $R^{11}$, $R^{14}$ and $R^{15}$ are independently hydrogen or a lower alkyl group or a group $X'-(R^{3'}O)_{a'}-R^{4'}-$ as hereinbefore defined wherein X' is —OH or a lower alkoxy group containing from 1 to 6 carbon atoms;

and $R^8$ and $R^{12}$, are independently alkyl groups containing from 1 to 4 carbon atoms and $R^9$ and $R^{13}$ and $R^{21}$ are independently a linear or branched chain alkylene bridging group containing from 1to 6 carbon atoms, $R^{16}$, $R^{17}$, $R^{18}$, $R^{19}$ and $R^{20}$ are independently hydrogen or a lower alkyl group and d is 0 or 1 and wherein a, is from 1 to 400 or if X is of formula IC, the sum of a, b and c is from 3 to 400.

A considerable number of salts of the compound of formula (I) suitable for use in agrochemical applications will occur to one skilled in the art. Examples of salts include phosphate, sulphate, carboxylate, acetate, formate and chloride although many other suitable salts will occur to one skilled in the art. Alternatively the compound of formula (I) may form a salt with an acidic agrochemical such as glyphosate. Salts of the compound of formula (I) can also be prepared from acidic surfactants, for example optionally ethoxylated alkyl or alkylene ester derivatives of phosphoric acid or phosphonic acid, or optionally ethoxylated alkyl or alkylene carboxylic acids or sulphonic acids. It will be appreciated that where more than one amine functionality is present in the compound of formula (I) or the relevant acid has more than one functional group, the option for different salt stoichiometries and mixed salts exists and all such variations are included herein.

As used herein, the term lower alkyl means a linear or branched chain primary or secondary alkyl group containing from 1 to 6 carbon atoms. Preferred lower alkyl groups contain from 1 to 4 carbon atoms, and methyl, ethyl and propyl or isopropyl groups are especially preferred.

$R^1$, $R^2$, $R^5$, $R^6$, $R^{10}$, $R^{11}$, $R^{14}$ and $R^{15}$ are preferably methyl or hydrogen. Hydrogen is especially preferred.

Thus it is preferred that in a compound of formula (I):—

X is —OH or a lower alkoxy group containing from 1 to 4 carbon atoms or

X is $R^5R^6N-$ wherein R5 and R6 are hydrogen or a lower alkyl group containing from 1 to 4 carbon atoms or X is a group of formula IC'

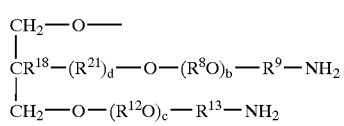

wherein $R^8O$ and $R^{12}O$ are independently ethoxy, or propoxy, in particular isopropoxy, or a random or block mixture thereof, $R^9$ and $R^{13}$ are independently a linear or branched chain alkylene bridging group containing 2 or 3 carbon atoms and $R^{21}$ is a linear or branched chain alkylene bridging group containing from 1 to 3 carbon atoms, $R^{18}$ is hydrogen or lower alkyl containing from 1 to 4 carbon atoms and d is 0 or 1, $R^1$ and $R^2$ are independently hydrogen or a lower alkyl group containing from 1 to 4 carbon atoms, $R^3O$ is ethoxy, or propoxy, in particular isopropoxy, or a random or block mixture thereof, $R^4$ is a linear or branched chain alkylene bridging group containing 2 or 3 carbon atoms and a is from 1 to 400 or if X is of formula IC', the sum of a, b and c is from 3 to 400.

The compounds for use in the composition of the present invention are alkoxylated monoamines (X is of Formula IA), diamines (X is of Formula IB) or triamines (X is of Formula IC). Alkoxylation typically takes place to introduce ethoxy groups or propoxy groups, although butoxy groups may sometimes also be used. The propoxy group is preferably an isopropoxy group, $—OCH_2—CH(CH_3)—$. Mixed alkoxylation may also take place to introduce for example both ethoxy and propoxy or butoxy groups which may be present as a mixture in either random or block arrangement. Thus each of $—(OR^3)_a—$, $—(OR^8)_b—$ and $—(OR^{12})_c—$ in the above formulae independently represent alkoxy groups, for example ethoxy and propoxy groups or a mixture thereof. Thus the definition of group $—(OR^3)_a$ for example includes a group

wherein a is represented by the sum of x and y. Other combinations of for example ethoxy propoxy and butoxy groups in any desired order are similarly included in the definition of $—(OR^3)_a—$, $—(OR^8)_b—$ and $—(OR^{12})_c—$ respectively.

The process of alkoxylation may produce a mixture of products having different degrees of alkoxylation. Thus the values of a, b, c and a' represent an average degree of alkoxylation over the product as a whole. Preferred values of a, b, and c, respectively are from 1 to 100, for example from 1 to 50 and especially from 1 to 30. Thus when X in formula (I) is of formula IC, the sum of a+b+c is preferably from 3 to 90. In the group $X'—(R^3O)_{a'}—R^{4'}—$ if present, a' is preferably from 0 to 50 and especially from 0 to 30.

An especially preferred alkoxylated monoamine (wherein X is of formula IA) for use in the present invention has the formula II wherein X is methoxy, $—(R^3O—)_a$ represents a mixture of ethoxy and propoxy groups $R^4$ represents a propylene bridging group.

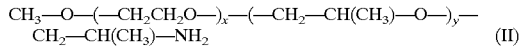

The average degree of ethoxylation (x) may vary from 0 to about 45 or more preferably from 0 to about 40, for example from 0 to about 20 and the average degree of propoxylation (y) may vary from 0 to about 90 and more preferably from about 1 to about 35, for example from about 2 to about 30, provided that x and y are not both 0 at the same time. Products are commercially available wherein x is about 1 and y is about 9; x is about 19 and y is about 3, x is about 6 and y is about 29 and x is about 32 and y is about 10. As specific examples of commercially available products there may be mentioned JEFFAMINE M600 (JEFFAMINE is a trade mark of Huntsman Limited) having an approximate molecular weight of 600 and a propoxy to ethoxy ratio of 9 to 1, JEFFAMINE M1000 having an approximate molecular weight of 1000 and a propoxy to ethoxy ratio of 3 to 19, JEFFAMINE M2005 having an approximate molecular weight of 2000 and a propoxy to ethoxy ratio of 29 to 6 and JEFFAMINE M2070 having an approximate molecular weight of 2000 and a propoxy to ethoxy ratio of 10 to 32.

Also included in the scope of the present invention is (i) diethylene glycolamine wherein in Formula I, X is OH, $(R^3O)$ is ethoxy, a is 1 and $R^4$ is an ethylene bridging group and $R^1$ and $R^2$ are hydrogen:

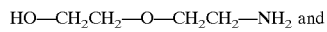

(ii) a compound of formula

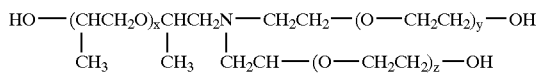

wherein in Formula I, X is $—OH$, $R^3$ and $R^4$ are isopropyl, $R^1$ and $R^2$ are $X'—(R^3{}'O)_{a'}—R^{4'}—$, X' is $—OH$, $R^{3'}$ and $R^{4'}$ are ethyl and x, y and z respectively take any of the values defined for a or a' as the case may be and (iii) a compound of formula

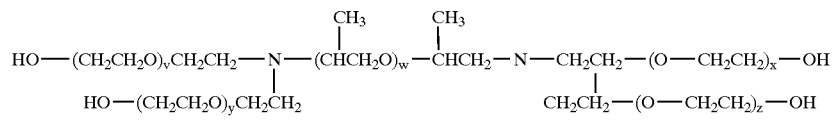

wherein in Formula I, X is $R^5R^6N—$, $R^3$ and $R^4$ are isopropyl, $R^1$, $R^2$, $R^5$ and $R^6$ are $X'—(R^3{}'O)_{a'}—R^{4'}—$, X' is $—OH$, $R^{3'}$ and $R^{4'}$ are ethyl and v, w, x, y and z respectively take any of the values defined for a or a as the case may be.

Also included in the scope of the present invention is tris 2-(2-methoxyethoxy)ethylamine wherein in formula I, X is $OCH_3$, $(R^3O)$ is ethoxy, a is 1 and $R^4$ is an ethylene bridging group and wherein $R^1$ and $R^2$ are each a group $—R^{4'}—(OR^3)_{a'}—X'$ wherein $(R^3{}'O)$ is ethoxy, a' is 1, $R^{4'}$ is an ethylene bridging group and X' is $OCH_3$.

An especially preferred propoxylated diamine (wherein X is of formula IB) for use in the present invention has the formula III wherein X is a group $H_2N—$, $—(R^3O—)_a$ represents propoxy groups $R^4$ represents a propoxy bridging group:

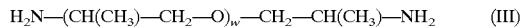

wherein w is an average of from about 1 to about 80. Products are commercially available wherein w is an average of about 2.6, 5.6, 33.1 and 68. As Examples of commercially available products of formula III, there may be mentioned JEFFAMINE D230 having an approximate molecular weight of 230 and a value of w of about 2.6, JEFFAMINE D400 having an approximate molecular weight of 400 and a value of w of about 5.6, JEFFAMINE D2000 having an approximate molecular weight of 2000 and a value of w of about 33.1, and JEFFAMINE D4000 having an approximate molecular weight of 4000 and a value of w of about 68. An especially preferred value for w is from about 2 to about 35, for example from about 2 to about 30.

An alternative diamine (wherein X is of formula 1B) having a mixture of ethoxylation and propoxylation for use in the present invention has the formula IV wherein X is a group $H_2N-$, $-(R^3O-)_a$ represents a mixture of ethoxy and propoxy groups $R^1$ and $R^2$ are hydrogen and $R^4$ represents a propylene bridging group:

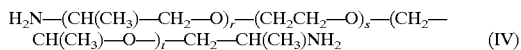
(IV)

wherein the sum of r+t (total propoxy content) is an average of from 1 to 20 propoxy groups, for example from about 1 to 10 propoxy units and s is an average of from 2 to 50 for example from 5 to 50 ethoxy units. Commercial products are available wherein the sum of r+t is about 3.6 and s represents an average of about 9, or 15.5 respectively or wherein r+t is about 6 and s represents an average of about 38.7. As examples of commercially available products of formula (IV) there may be mentioned JEFFAMINE ED 600 having an approximate molecular weight of 600 and an propoxy to ethoxy ratio of 3.6 to 9, JEFFAMINE ED 900 having an approximate molecular weight of 900and an propoxy to ethoxy ratio of 3.6 to 15.5 and JEFFAMINE ED 2003 having an approximate molecular weight of 2000 and an propoxy to ethoxy ratio of 6.0 to 38.7. It is especially preferred that the value of (r+t) is from about 2 to about 15 and s is from about 3 to about 20.

An especially preferred propoxylated triamine (wherein X is formula IC) has the formula (V)

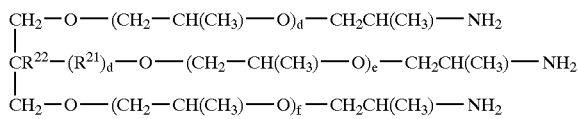
(V)

wherein the sum of d+e+f is an average of from about 5 to 90 and $R^{22}$ is hydrogen or lower alkyl containing 1 to 4 carbon atoms such as methyl or ethyl, $R^{21}$ is a linear or branched chain alkylene bridging group containing from 1 to 3 carbon atoms and d is 0 or 1. Products are available commercially wherein the sum of d+e+f is about 5.6, about 50 and about 85 respectively. Thus as examples of commercially available products of formula (V) there may be mentioned JEFAMINE T403 having an approximate molecular weight of 440 and a value of d+e+f (total propoxy content) of 5.6, JEFAMINE T3000 having an approximate molecular weight of 3000 and a value of d+e+f (total propoxy content) of 50 and JEFAMINE T5000 having an approximate molecular weight of 5000 and a value of d+e+f (total propoxy content) of 85.

We have found that the activity enhancing effect of the adjuvants in the composition of the present invention is particularly and surprisingly marked when the agrochemical active ingredient is water-soluble. The agrochemical for use in the composition of the present invention is preferably a water-soluble electrolyte such as an agrochemical salt and in particular a herbicidally active agrochemical salt for example a salt of glyphosate, paraqua or fomesafen. Typical of the commonly available salts of glyphosate are the isopropylamine, trimethylsulphonium, sodium, potassium, ammonium, and ethanolamine salts. Paraquat is generally sold in the form of paraquat dichloride. Fomesafen is generally formulated as the sodium salt.

The proportion of adjuvant of formula (I) to agrochemical, for example glyphosate (expressed as the acid) may vary within wide ranges depending on the desired level of activation. Typically the proportion of adjuvant of formula (I) to agrochemical will be from 1:40 to 3:1 for example from 1:20 to 3:1 by weight and especially from 1:10 to 1:1 by weight.

The compositions of the present invention may be used on their own but are preferably used in the form of a composition containing a carrier comprising a solid or liquid diluent.

Compositions of the invention include both dilute compositions, which are ready for immediate use, and concentrated compositions, which require to be diluted before use, usually with water. The concentration of the composition will depend on the nature of the active ingredient. Typically, and especially for example if the active ingredient is a herbicide, the compositions contain from 0.01% to 90% by weight of the active ingredient. Dilute compositions ready for use preferably contain from 0.01 to 2% of active ingredient, while concentrated compositions may contain from 20 to 90% of active ingredient, although from 20 to 70 is usually preferred.

The solid compositions may be in the form of granules, or dusting powders wherein the active ingredient and adjuvant are mixed with a finely divided solid diluent, e.g. kaolin, bentonite, kieselguhr, dolomite, calcium carbonate, talc, powdered magnesia, Fuller's earth and gypsum. In some instances, and in particular when the active ingredient is glyphosate, inorganic salts such as ammonium sulphate may be used both as adjuvant and solid support. They may also be in the form of dispersible powders or grains, comprising a wetting agent to facilitate the dispersion of the powder or grains in liquid. Solid compositions in the form of a powder may be applied as foliar dusts.

The rate of application of the compositions of the invention will depend on a number of factors depending in particular on the nature of the active ingredient. When the active ingredient is a herbicide, such factors include, the compound chosen for use, the identity of the plants whose growth is to be inhibited, the formulations selected for use and whether the compound is to be applied for foliage or root uptake. As a general guide, however, an application rate of from 0.001 to 20 kilograms active ingredient per hectare is suitable while from 0.025 to 10 kilograms per hectare may be preferred.

The adjuvant of formula (I) or a mixture of different adjuvants of formula (I) may be used as the sole adjuvant to enhance the biological activity or physical properties of the agrochemical or may alternatively be used in conjunction with one or more additional adjuvants. The adjuvant of formula (I) may for example be combined with cationic surfactants, anionic surfactants, amphoteric surfactants or non-ionic surfactants. Such surfactants are well known in the art but as surfactants which are particularly well suited to be combined with an adjuvant of formula (I) there may be mentioned alkyl glycosides (mono and poly), alcohol ethoxylates, alkyl phenol ethoxylates, alkyl ester ethoxylates, sorbitan ester ethoxylates, siloxane ethoxylates, acetylenic diol ethoxylates, optionally alkoxylated tertiary or quaternary alkyl amines, optionally alkoxylated alkyl amine oxides, alkyl betaines optionally alkoxylated alkyl phosphate esters and sucrose alkyl esters. The adjuvant of formula (I) may also be combined with other activity-enhancing adjuvants, for example ammonium sulphate, urea or humectants, such as glycerol, polyethylene glycol, sorbitol, ethylene glycol, propylene glycol and lactate salts.

Certain of the adjuvants for use in the composition of the present invention have surprisingly low surface activity (high surface tension) as compared with conventional agrochemical adjuvants. These adjuvants with low surface activity generally exhibit a more favourable toxicological profile.

Surface tension of the adjuvants for use in the present invention was measured as a 0.2% w/v solution in deionised water adjusted to pH 4 with hydrochloric acid at 20° C., and preferred adjuvants such as JEFFAMINE ED600 ED900 and D400 have a surface tension measured by this method of greater than 50 mNm$^{-1}$ as compared with AGRIMUL PG2067 alkylpolyglycoside which has a surface tension measured by this method of 28 mNm$^{-1}$. Adjuvants having a surface tension of less than 50 mNm$^{-1}$ also give excellent results and JEFFAMINE D2000 for example having a surface tension measured by this method of 42 mNm$^{-1}$ may even provide advantages on certain weed species as discussed below.

Compositions of the present invention generally exhibit excellent low-foaming properties when the composition is incorporated in the spray tank and during transportation and spraying.

When the active ingredient is a herbicide and in particular a water-soluble herbicide, adjuvants of formula (I) generally provide excellent and effective enhancement of activity in respect of most important weed species encountered in the field. Enhancement may however be less marked on certain "difficult" weed species. We have found that the use of a mixture of an adjuvant of formula (I) with a surfactant and in particular with an alkylpolyglycoside surfactant may provide excellent enhancement of activity both against normal weed species and against "difficult" species. Indeed in certain circumstances synergy may be observed and greater enhancement of control of "difficult" species may be obtained than when using either the adjuvant of formula (I) or the alkylpolyglycoside alone. The ratio of the adjuvant of formula (I) to the alkylglycoside is preferably from 1:40 to 4:1, for example 1:20 to 4:1, especially from 1:6 to 2:1 and most preferably about 1 to 1.

When the active ingredient is a herbicide, the invention provides, in a further aspect, a process for severely damaging or killing unwanted plants, which process comprises applying to the plants, or to the growth medium of the plants, a herbicidally effective amount of a composition as hereinbefore defined.

The invention is illustrated by the following Examples in which all parts and percentages are by weight unless otherwise stated.

EXAMPLES 1 to 10

Potassium glyphosate was applied at 500 g glyphosate acid equivalent/ha to *Abutilon theophrasti* (ABUTH) plants grown in the glass-house. All treatments were made up in deionised water and applied using a tracksprayer with a 11002 nozzle at a spray application volume of 200 l/ha. All treatments were replicated 4 times. After spraying the plants were laid out in a glass-house and maintained at a temperature of 24° C. by day and 19° C. by night. The JEFFAMINE adjuvants were used in a proportion 0.2% w/v. A visual assessment of % control, where 0=unaffected and 100=complete kill, was carried out 16 days after treatment.

| Example No | Treatment | % control |
| --- | --- | --- |
| Comparison | No adjuvant | 37 |
| 1 | JEFFAMINE D400 | 93 |
| 2 | JEFFAMINE D2000 | 76 |
| 3 | JEFFAMINE T3000 | 79 |
| 4 | JEFFAMINE ED600 | 89 |
| 5 | JEFFAMINE ED900 | 85 |

-continued

| Example No | Treatment | % control |
| --- | --- | --- |
| 6 | JEFFAMINE ED2003 | 85 |
| 7 | JEFFAMINE M600 | 85 |
| 8 | JEFFAMINE M1000 | 81 |
| 9 | JEFFAMINE M2005 | 70 |
| 10 | JEFFAMINE M2070 | 74 |

EXAMPLES 11 TO 14

Potassium glyphosate was applied to *Abutilon theophrasti* (ABUTH), *Brassica napus* (BRSNS) and *Veronica persica* (VERPE) drilled as rows in the field, at a spray application volume of 200 l/ha. The indicated adjuvant was included in the formulation at a total adjuvant concentration of 0.2% w/v. Application rates were 150,300 and 450 g glyphosate acid/ha and each treatment was replicated 3 times. Data (mean of the three replicates and across all rates) is presented for a visual assessment of % control carried out at 26 days after application (DAA), where 0=unaffected and 100%=complete kill.

AL2042 is an alkylpolyglycoside surfactant based on the same alkylpolyglycoside as AGRIMUL PG2067. Both JEFFAMINE ED600 and JEFFAMINE D400 showed excellent adjuvant activity on representative species ABUTH and VERPE. On the "difficult" species BRSNS, the combination of the JEFFAMINE adjuvant and the alkylpolyglycoside showed greater activity than either the JEFFAMINE adjuvant or the alkylpolyglycoside on its own.

| Example No | Total adjuvant = 0.2% | ABUTH | BRSNS | VERPE |
| --- | --- | --- | --- | --- |
| 11 | JEFFAMINE ED600 | 70.0 | 64.7 | 48.8 |
| 12 | JEFFAMINE D400 | 64.9 | 62.2 | 47.2 |
| 13 | JEFFAMINE ED600 and Agrimul PG2067 (0.1% + 0.1%) | 57.8 | 78.9 | 44.4 |
| 14 | JEFFAMINE D400 and Agrimul PG2067 (0.1% + 0.1%) | 57.7 | 77.1 | 44.7 |
| Comparison | AL2042 | 45.8 | 70.3 | 39.7 |

EXAMPLE 15

This Example illustrates the use of a salt of ethoxy (5 moles of EO) isotridecyl phosphate, ester in the acid form (CRODAFOS T5A) with JEFFAMINE ED600. CRODAFOS T5A is a mixture of mono and di esters. CRODAFOS is a tradename of Croda.

Potassium glyphosate, in combination with the adjuvants specified below, was applied to *Ipomoea hederacea* (IPOHE) at 300 g glyphosate acid equivalent/ha. All treatments were made up in deionised water and applied using a tracksprayer with a 11002 nozzle at a spray application volume of 200 l/ha. All treatments were replicated 4 times. After spraying the plants were laid out in a glass-house and maintained at a temperature of 24° C. by day and 19° C. by night. A visual assessment of % control was carried out 16 days after treatment.

| Treatment | IPOHE — % control |
|---|---|
| No adjuvant | 64 |
| AL2042 | 71 |
| CRODAFOS T5A, JEFFAMINE ED600 salt | 86 |
| CRODAFOS T5A, potassium salt | 79 |

The AL2042 was applied at 0.2% w/v and the CRODAFOS T5A salts were applied at 0.2% w/v phosphate ester acid equivalent. The Crodafos T5A potassium salt was prepared by neutralising the phosphate ester in its acid form with potassium hydroxide to pH6. The CRODAFOS T5A JEFFAMINE ED600 salt was prepared by neutralising the phosphate ester in its acid form with JEFFAMINE ED600 to pH6.

EXAMPLE 16

This Example illustrates the use of salts of glyphosate acid and the adjuvants of Formula (I).

Glyphosate trimesium and the glyphosate salts of the indicated adjuvants of formula (I) were applied to *Soghinm halepenise*(SORHA) at 500, 1000, 2000 and 4000 glyphosate acid equivalent/ha. All treatments were made up in deionised water and applied using a tracksprayer with a 11002 nozzle at a spray application volume of 200 l/ha . All treatments were replicated 3 times. After spraying the plants were laid out in a glass-house and maintained at a temperature of 24° C. by day and 19° C. by night. A visual assessment of % control was carried out 22 days after treatment and calculated doses for 90% control (ED90) were derived. AL2042 alkylpolygylcoside was used at 0.25% w/v as additional surfactant with all treatments. It will be appreciated that a low ED90 value indicates high activity.

| Glyphosate salt | Adjuvant | SORHA — ED90 gae/ha |
|---|---|---|
| Glyphosate trimesium | AL2042 | 1410 |
| Glyphosate JEFFAMINE D400 | AL2042 | 821 |
| Glyphosate JEFFAMINE M600 | AL2042 | 493 |

EXAMPLE 17

Paraquat dichloride, in combination with the adjuvants specified below, was applied to Abutilon theophrasti (ABUIH) at four rates of paraquat (15, 45, 135 and 270 g/ha paraquat ion). All treatments were made up in deionised water and applied using a tracksprayer with a 11002 nozzle at a spray application volume of 200 l/ha. All treatments were replicated 3 times. After spraying the plants were laid out in a glass-house and maintained at a temperature of 22° C. by day and 18° C. by night. A visual assessment of % control was carried out 18 days after treatment and calculated doses for 90% control (ED90-g paraquat ion per litre) were calculated. The adjuvants were applied at 0.1% w/v.

| Treatment (0.1% adjuvant) | ABUTH | SIDSP |
|---|---|---|
| Control — No adjuvant | 325 | (>270) |
| JEFFAMINE ED600 | 246 | 182 |

What is claimed is:

1. An agrochemical composition comprising an agrochemical active ingredient and an adjuvant of formula (I) and salts thereof $$X—(R^3O)_a—R^4—NR^2R^1 \quad (I)$$

wherein $R^1$ and $R^2$ are independently hydrogen or a lower alkyl group containing from 1 to 4 carbon atoms, $R^3O$ is an ethoxy, propoxy or butoxy group or a random or block mixture thereof, $R^4$ is a linear or branched chain alkylene bridging group containing from 1 to 4 carbon atoms, X is (IA) —OH or a lower alkoxy group containing from 1 to 4 carbon atoms or X is (IB) a group $R^5R^6N—$ wherein $R^5$ and $R^6$ are independently hydrogen or a lower alkyl group containing from 1 to 4 carbon atoms or X is (IC) a group

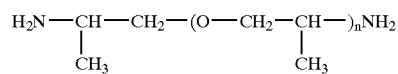

wherein $R^8O$ and $R^{12}O$ are independently ethoxy, or propoxy or a random or block mixture thereof, $R^9$ and $R^{13}$ are independently a linear or branched chain alkylene bridging group containing 2 or 3 carbon atoms, $R^{21}$ is a linear or branched chain alkylene bridging group containing from 1 to 3 carbon atoms, $R^{18}$ is hydrogen or lower alkyl containing from 1 to 4 carbon atoms, d is 0 or 1, and wherein a, is from 1 to 400 or if X is of formula IC, the sum of a, b and c is from 3 to 400, provided that when X is of formula (1B), the adjuvant of formula (1 ) does not have the structure

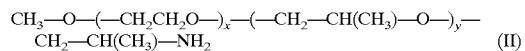

wherein n is 2 or 3.

2. A composition according to claim 1 wherein a is from 1 to 50 or if X is of formula IC, the sum of a, b and c is from 3 to 90.

3. A composition according to claim 1 wherein the adjuvant of formula (I) is an alkoxylated monoamine, having the formula II $$CH_3—O—(—CH_2CH_2O—)_x—(—CH_2—CH(CH_3)—O—)_y—CH_2—CH(CH_3)—NH_2 \quad (II)$$

wherein the average degree of ethoxylation (x) is from 0 to about 45 and the average degree of propoxylation (y) is from 0 to about 90 provided that x and y are not both 0 at the same time.

4. A composition according to claim 3 wherein the value of x is from 0 to about 20 and of y is from about 2 to about 30.

5. A composition according to claim 1 wherein the compound of formula (I) is a diamine having a formula (II)

$$H_2N—(CH(CH_3)—CH_2—O)_w—CH_2—CH(CH_3)—NH_2 \quad (III)$$

wherein w is an average of from about 1 to about 80.

6. A composition according to claim 5 wherein w is an average of from about 2 to about 35.

7. A composition according to claim 1 wherein the compound of formula (I) is a diamine having a formula (IV)

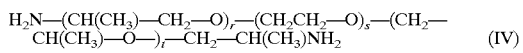

wherein the sum of r+t is an average of from 1 to 20 propoxy groups and s is an average of from 2 to 50 ethoxy units.

8. A composition according to claim 7 wherein the sum of r+t is from about 2 to about 15 and s is from about 3 to about 20.

9. A composition according to claim 1 wherein the compound of formula (I) is a propoxylated triamine having the formula (V)

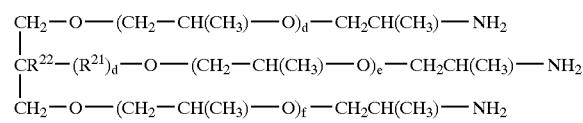

wherein the sum of d+e+f is an average of from about 5 to 90, $R^{22}$ is hydrogen or lower alkyl containing 1 to 4 carbon atoms, $R^{21}$ is a linear or branched chain alkylene bridging group containing 1 to 3 carbon atoms and d is 0 or 1.

10. A composition according to claim 1 wherein the proportion of adjuvant of formula (I) to the agrochemical is from 1:20 to 3:1 by weight.

11. A composition according to claim 1 wherein the adjuvant of formula (I) in claim 1 is used in combination with an alkylpolyglycoside surfactant.

12. A composition according to claim 11 wherein the ratio of the adjuvant of formula (I) to the alkylpolyglycoside surfactant is from 1:40 to 4:1.

13. A composition according to claim 1 wherein the agrochemical active ingredient is a salt of glyphosate, a salt of fomesafen or a paraquat salt.

14. A composition according to claim 1 (wherein the adjuvant of formula (I) in claim 1 is used in the form of a salt with glyphosate or a salt with an acidic surfactant.

15. A process of severely damaging or killing unwanted plants which process comprises applying to the plants or to the growth medium of the plants, a herbicidally effective amount of a composition as claimed in claim 1.

16. A composition according to claim 1 which is an aqueous composition containing from 0.01% to 90% by weight of the active ingredient.

* * * * *